US005703195A

United States Patent [19]
Schultz et al.

[11] Patent Number: 5,703,195
[45] Date of Patent: Dec. 30, 1997

[54] POLYGLYCIDYLPHENYL ETHERS OF ALKYLENE OR ALKYLENEOXY CHAINS FOR USE IN MICROELECTRONICS ADHESIVES

[75] Inventors: Rose Ann Schultz, Princeton; Steven P. Fenelli, Hillsborough, both of N.J.

[73] Assignee: National Starch and Chemical Investment Holding Corporation, Wilmington, Del.

[21] Appl. No.: 757,187

[22] Filed: Nov. 27, 1996

Related U.S. Application Data

[60] Division of Ser. No. 656,597, May 31, 1996, Pat. No. 5,646,315, which is a continuation-in-part of Ser. No. 482,541, Jun. 7, 1995, abandoned.

[51] Int. Cl.⁶ .......................... C08L 63/00; C07D 303/28
[52] U.S. Cl. ........................... 528/103; 528/117; 549/554
[58] Field of Search ............................ 528/103, 117; 549/554

[56] References Cited

U.S. PATENT DOCUMENTS

| 3,522,210 | 7/1970 | Sellers et al. ........................ 260/47 |
| 4,110,354 | 8/1978 | Bertram et al. .................. 260/348.14 |
| 5,536,855 | 7/1996 | Schultz et al. ...................... 549/539 |

FOREIGN PATENT DOCUMENTS

| 0 028 024 A1 | 5/1981 | European Pat. Off. ....... C07D 303/16 |
| 0 028 024 | 6/1981 | European Pat. Off. ....... C07D 303/16 |
| 0 205 402 | 12/1986 | European Pat. Off. ....... C07D 303/24 |
| 0 205 402 A2 | 12/1986 | European Pat. Off. ....... C07D 303/24 |
| 0 272 442 A2 | 6/1988 | European Pat. Off. ......... C08G 59/32 |
| 0 397 317 | 11/1990 | European Pat. Off. ....... C07D 303/24 |
| 0 397 317 A1 | 11/1990 | European Pat. Off. ....... C07D 303/24 |
| 0 459 591 | 4/1991 | European Pat. Off. ......... C08G 59/38 |
| 0 459 591 A2 | 12/1991 | European Pat. Off. ......... C08G 59/38 |
| 0 747 370 A1 | 11/1996 | European Pat. Off. ....... C07D 303/28 |
| 0 747 371 A1 | 11/1996 | European Pat. Off. ....... C07D 303/46 |
| 1017612 | 1/1963 | United Kingdom . |
| WO 95/23794 | 8/1995 | WIPO .......................... C07D 303/16 |

*Primary Examiner*—Donald R. Wilson
*Attorney, Agent, or Firm*—Jane E. Gennaro

[57] ABSTRACT

This invention relates to flexible epoxy resins characterized by a low ionic contamination, total chlorine content less than 0.1%. The epoxy resins are liquids at room temperature, have Tg values when cured of less than or equal to 150° C., have neat resin viscosities of 25,000 cps or less at 25° C., and have a structural composition comprising an oligomeric backbone of alkylene repeat units, terminated with an aromatic moiety bearing one or more epoxy functionalities. The flexible epoxy resins are used in adhesives for microelectronic applications.

3 Claims, No Drawings

5,703,195

POLYGLYCIDYLPHENYL ETHERS OF ALKYLENE OR ALKYLENEOXY CHAINS FOR USE IN MICROELECTRONICS ADHESIVES

This application is a division of application Ser. No. 08/656,597, filed May 31, 1996, now U.S. Pat. No. 5,646,315, which is a continuation-in-part of Ser. No. 08/482,541, filed Jun. 7, 1995, abandoned.

FIELD OF THE INVENTION

This invention is directed to flexible epoxy compounds for use in microelectronics adhesives that can be rapidly cured and that have low or no ionic contamination, and to processes for their syntheses.

BACKGROUND OF THE INVENTION

One step in the manufacture of semiconductor integrated circuits is the bonding of a silicon chip or die with an adhesive to a copper frame from which extend metal conductor leads. The bonded die and lead frame assembly is encapsulated within a polymeric sealant and connected to external circuitry by way of the metal conductor leads that extend through the encapsulation.

Epoxy compounds are preferred as the die attach or encapsulating adhesive due to their superior adhesive strength. The epoxies conventionally used are the aromatic epoxies, due to their strength, but these are inherently rigid and brittle. During the manufacturing process the adhesives and substrates are subjected to repeated thermal cycling. If the adhesives and substrates have widely disparate coefficients of thermal expansion, the stress of thermal cycling can lead to adhesive failure, substrate warpage, or fracture of the die. Thus, a crucial requirement for an adhesive destined for microelectronics use is that it be strong and flexible to absorb the stress of thermal cycling.

A second crucial criterion is that the adhesives be capable of rapidly curing to meet the speeds of assembly line processing. The fast cure times required, typically 30–60 seconds at about 200° C., are known as snap-cure. This combination of criteria, adhesive strength, flexibility, and ability to be snap-cured, is difficult to attain in one adhesive.

It is also crucial that the epoxy formulations be free of ionic contamination, particularly sodium and chloride ions, and free of bonded chlorine. These contaminants can cause corrosion of the metal leads in semiconductor devices and the ultimate failure of the devices.

To add flexibility, epoxies can be co-reacted with an aliphatic flexibilizer; this, however, reduces adhesive strength because the level of aromatic moieties is lowered. The addition of a flexibilizer also reduces the ability of the adhesive to be snap-cured because the flexibilizer has a high molecular weight per epoxy. Moreover, when the aliphatic and aromatic epoxies are cured, they may not co-react due to a difference in reactivity rates; low molecular weight compounds may volatilize out before cure, and high molecular weight compounds may not completely cure. This combination of factors, sometimes even a problem for slow cure formulations, is fatal for achieving snap-cure.

As a possible solution to some of these problems, it is known to combine aromatic moieties with aliphatic moieties in the backbone of the same polymer, but the currently available polymers of this type have a high ratio of aromatic to aliphatic moieties, which results in a loss of flexibility. Additionally, the method of preparation of these materials results in high chlorine contamination, which is deleterious in microelectronics applications. The polymers also have high viscosities, which requires the addition of a solvent as a diluent. During snap-cure, the curing is sometimes faster than complete solvent volatilization, which leads to voids in the cured adhesive, and potential failure of the microelectronics chip or device. Thus, low viscosity materials, which eliminate the need for solvent, are preferred.

The problems associated with providing strength to flexible compounds, and with snap-cure, are amplified as the microelectronics industry moves toward larger and larger die sizes. This creates a continuing need for improved flexible epoxies, which have strength and purity, and that can be formulated into snap-cured die attach adhesives.

SUMMARY OF THE INVENTION

This invention relates to flexible epoxy resins that can be used to formulate snap-curable die attach adhesives, encapsulants, and coatings. The epoxies are prepared by a synthetic route that avoids the use of epichlorohydrin resulting in low levels of ionic contaminated sources (including sodium ion, chloride ion, and organic bound chlorine), less than about 0.1% by weight, compared to prior art compositions, which contain impurities at higher levels, especially when the compositions are not subjected to stringent purification methods that significantly reduce yields. Moreover, the synthetic routes permit the preparation of discreet chemical structures, rather than mixes of various resins.

The epoxy resins are liquids at room temperature, have Tg values when cured of less than or equal to 150° C., and have neat resin viscosities of 25,000 cps or less at 25° C. Thus, no solvent is required for formulating these epoxies into highly filled adhesives (for example, with thermal or conductive fillers).

The modulus of elasticity, percent strain and glass transition temperature ($T_g$) values for these epoxies indicate high flexibility. The modulus typically is less than or equal to 2.0 MPa. The percent strain typically is greater than or equal to 5%. The cured $T_g$ values for these epoxies will be 150° C. or less, and for some compounds will be 100° C. or less.

In another embodiment, this invention pertains to adhesives made with these epoxies, for use in microelectronics applications. The flexibility of these compounds is retained when the epoxies are formulated with conductive material, such as silver flakes, and used to bond silicon chips to a metal lead frame substrate. The cured epoxies demonstrate a high radius of curvature, greater than or equal to 350 mm. (The higher the radius of curvature, the less chip warpage, which in turn implies a flexible adhesive.)

The cured epoxies also demonstrate good adhesive strength, measured as die shear strength. Die shear is a measure of the force required to remove a bonded chip from the metal substrate, which for these compounds is greater than or equal to 13 MPa.

Moreover, the adhesives exhibit no loss of flexibility or strength. Preferably the formulation will comprise 20–80 parts by weight of the flexible epoxy and 80–20 parts of an aromatic O-glycidyl ether (to a total of 100 parts), a curing agent, a conductive filler, and optionally 20–50 parts of a phenolic hardener per hundred parts of epoxy resin (pphr).

DETAILED DESCRIPTION OF THE INVENTION

The structural composition of the epoxy resins comprises an oligomeric backbone of alkylene or alkyleneoxy repeat units, of moderate length to provide flexibility, but still maintain sufficient crosslink density to yield useful adhesive properties. The flexible backbone is terminated on one or both ends with an aromatic moiety bearing one or more epoxy functionalities. Thus, the compounds have no more than two aromatic moieties, which exist only at the termini. Restricting the number and the location of aromatic moieties in the polymer backbone maintains the strength imparted to the cured material by the aromatic moieties and maximizes the flexibility imparted to the cured material by the aliphatic moieties.

The compounds have no more than two hydroxyl groups per molecule; restricting the number of hydroxyl groups to two or less promotes low viscosity.

The epoxies have one of the following general structural formulas:

the OH of the carboxyl group is replaced by some other substituent, in this case, the phenyl ring to which it is attached.

The flexibilized epoxy resins may be prepared by any suitable synthetic method that leaves the product free of ionic contamination. The preferred synthetic routes are those that avoid the use of epichlorohydrin, and comprise the steps of (a) preparing an olefinic precursor by attaching an alkylene or alkyleneoxy chain to a phenoxy compound bearing olefinic groups, and (b) oxidizing the olefinic groups to the corresponding epoxides.

In step (a), the flexible alkylene or alkyleneoxy chain is end terminated with a functional group that is activated toward nucleophilic substitution. Preferably the functional group is an epoxy, chloro, sulfonate, or toluenesulfonate. The flexible chain is derivatized by nucleophilic addition of a phenolate compound displacing the chloride, sulfonate, or

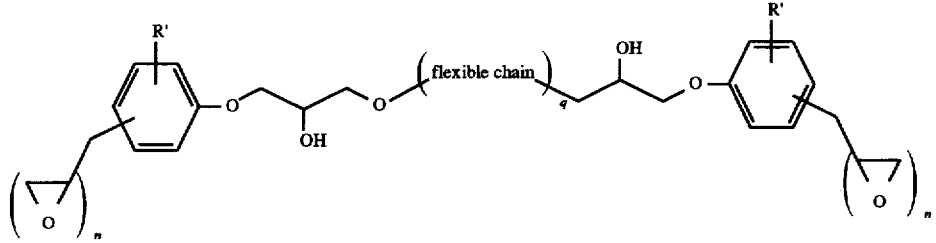

I.

where flexible chain is CH2CH2CH2CH2O when q=1–6
or where flexible chain is CH2CH2O when q=3–10 alkoxide (from epoxy ring opening) functional group. The phenolate is prepared from the reaction of sodium hydroxide

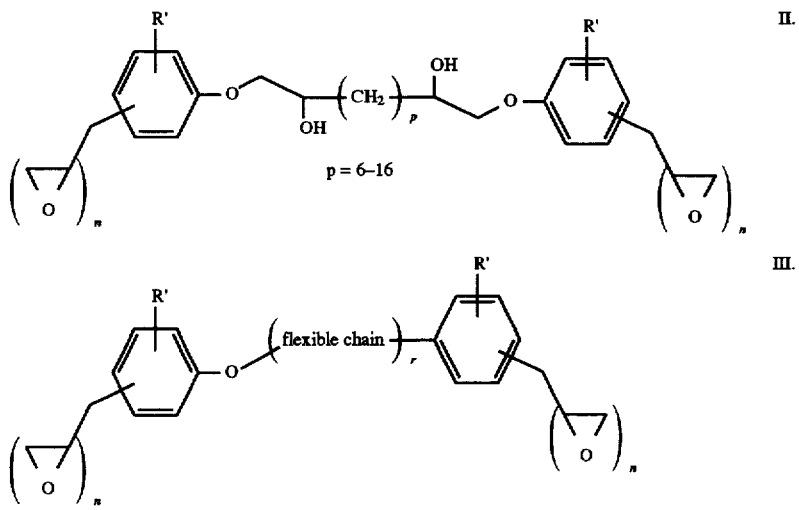

II.

III.

where flexible chain is CH2CH2CH2CH2O when r=1–10
or where flexible chain is CH2CH2O when r=3–10
or where flexible chain is CH2 when r=10–20
in which R' is H, $C_{1-18}$ alkyl, $C_{1-5}$ alkoxy or aryl or alkylaryl, $C_{1-5}$ perfluoroalkyl, or $C_{1-5}$ acyl; n is an integer 1–3; the flexible chain is as described for each structure; and p, q, and r am integers as described for each structure.

As used here, alkyl refers to a hydrocarbon group derived from an alkane and have the generic formula $C_nH_{2n+1}$; alkoxy refers to an alkyl group also containing oxygen; aryl refers to a group having the ring structure characteristic of benzene; alkylaryl refers to a group containing both alkyl and aryl structures; perfluoroalkyl refers to an alkyl group in which one or more of the hydrogens are substituted with fluorine; and acyl refers to an organic acid group in which or other alkali metal hydroxide with a phenol compound having only one hydroxyl group, which assures that the nucleophilic substitution can occur only once and discrete chemical structures result (that is, not mixtures of products). The phenol compound is also substituted with an olefin moiety, preferably an allyl group, which is inert to nucleophilic substitution, and serves as the site for the final epoxide product. In step (b), the olefin on the phenol group is converted to the oxirane (epoxide).

Preparation of the Olefinic Precursors

The olefinic precursors to the epoxy compound preferably may be prepared by one of the following generally described methods. More specific detail for each method is provided in the examples.

I. A diglycidyl compound of an alkylene or alkyleneoxy chain, of appropriate length to conform in the final product to one of the above described general structures, may be reacted with a phenolic compound bearing one or more olefinic groups in the presence of a catalyst effective for catalyzing condensation reactions between phenolic compounds and oxiranes.

Preferred diglycidyl compounds are 1,4-butanediol diglycidyl ether; 1,12-dodecanediol diglycidyl ether; polyethylene glycol digylcidyl ether, poly(tetra-methylene glycol) diglycidyl ether, and polypropylene glycol diglycidyl ether in which the polyglycol portion of the molecule has a molecular weight less than or equal to 2000 daltons; 1,2,9, 10-diepoxydecane, 1,2,13,14-diepoxytetradecane, and similar compounds; and the diglycidyl ether of poly (caprolactone)diol.

Preferred olefin functionalized phenolic compounds are 2-allylphenol; 2,6-diallylphenol; 2,4-diallylphenol; 4-allyl-2-methoxyphenol; and other similar phenolic compounds. The phenolic compound can be used in excess to effect a high degree of reaction with the diglycidyl compound and the excess can be removed from the product by distillation. The phenolic compound may also be substituted with groups that do not interfere with either of the two steps involved in the formation of the product.

Preferred catalysts are quaternary ammonium or phosphonium salts of chloride, bromide, hydrogen sulfate, acetate, and other known catalysts, such as, triphenylphosphine. More preferred catalysts are the quaternary ammonium salts with lower alkyl constituents, particularly tetramethyl ammonium chloride.

II. An alkylene or alkyleneoxy chain, of appropriate length to conform in the final product to one of the above described general structures, and bearing a leaving group, such as, chloride, bromide, iodide, or tosylate, at the termini of the chain, may be reacted with an alkali or alkaline earth metal salt of a phenoxide compound bearing olefinic groups.

The alkylene or alkyleneoxy compound bearing the leaving group generally is derived from the corresponding alcohol by conversion of the hydroxyl group into a leaving group using known reactions. For example, an alkylene or alkyleneoxy chloride can be generated from the alcohol by reaction with $SOCl_2$. The tosylate can be generated from the alcohol by reaction with tosyl chloride in the presence of base. Examples of suitable alcohol terminated alkylene or alkyleneoxy chains include 1,4-butanediol; 1,12-dodecanediol; polycaprolactone diol; polyethylene glycol; and 1,10-decanediol.

The olefin functionalized phenoxide compound is generated from the corresponding phenolic compound by the action of an alkali or alkaline earth metal hydroxide in the presence of an azeotroping solvent. These reactions are well known in the art. Suitable azeotroping solvents include toluene, xylene, p-cymene, and similar solvents.

Epoxidation of the Olefinic End Groups

After the precursors are formed, the olefin in oxidized by any method effective to provide the corresponding epoxy. Various methods are described in the literature for effectively carrying out the oxidation process, and include the use as an oxidant of organic peracids, such as peracetic acid or trifluroperacetic acid; peroxyimidic acids; dioxirane compounds like dimethyldioxirane; inorganic peracids, such as peroxytungstate systems; metal-catalyzed systems, such as methyltrioxorhenium and hydrogen peroxide, titanium catalyzed t-butyl-hydroperoxide, and manganese-salen catalyzed oxidations.

The preferred epoxidation methods use inorganic peracids, peracetic acid, and peroxyimidic acids as the primary oxidant. More specific detail for each method is provided in the examples.

The preferred inorganic peracids are based on tungstic acid, phosphotungstic acid, and similar compounds, using hydrogen peroxide as the secondary oxidant. The oxidation process is enhanced by employing a two phase system and a quaternary ammonium or phosphonium salt as the phase transfer catalyst.

Peracetic acid in acetic acid may also be used successfully as the oxidant. Although many solvents are suitable for this oxidation, the rate is faster in chlorinated solvents, such as, dichloroethane. In this process, as the reaction is pushed to complete conversion, the accumulating acetic acid begins to attack the oxirane. The result is a product with a lower oxirane content (higher WPE), and higher viscosity than if the oxidizing agent is an inorganic peracid in the presence of a quaternary onium salt.

The use of peroxyimidic acid as the oxidant provides the advantage that the byproduct is acetamide, which is innocuous to the oxirane. A preferred peroxyimidic acid is derived from acetonitrile and hydrogen peroxide. The optimum conditions for the peroxyimidic acid oxidation include the use of $KHCO_3$, reaction temperature near 40° C., and optionally, the use of an aqueous sponge, such as, 2,2-dimethoxypropane.

Formulation of Snap-Cure Adhesives

The flexible epoxy compositions of this invention are useful as oven cured adhesives; however, their utility can be expanded if the snap-cure property is available. The epoxies can be formulated into adhesives that exhibit good adhesive strength, flexibility, and ability to be snap-cured. The preferred formulations will contain 20–80 parts by weight of the flexible epoxy and 80–20 parts by weight of an aromatic O-glycidyl ether resin (to total 100 parts), a curing catalyst, and optionally one or more fillers. In general the curing catalyst is an imidazole catalyst, present in an amount of about 5–10 parts per hundred parts resin, and the filler is thermally or electrically conductive, such as silver flakes, although other electrically or thermally conductive fillers or silica may be used. The filler is preferably present in an amount of about 25% by volume of the adhesive formulaton.

The aromatic O-glycidyl ether (aromatic epoxy) will be substituted with one or more aromatic rings, and optionally with one or more $C_1$–$C_3$ groups. The aromatic epoxies will have an epoxy equivalent weight (WPE, weight per epoxy) of 200 or less, and will be derived form the corresponding phenolic hardeners. Exemplary aromatic epoxies are bisphenol-Fdiglycidyl ether, bisphenol-A diglycidyl ether, resorcinol diglycidyl ether, and the epoxy phenol novolaks.

The adhesive formulation may further contain 20–50 parts per hundred parts of resin of a phenolic hardener having one or more hydroxyl groups per aromatic ring (from which are derived the aromatic epoxies described above). Exemplary phenolic hardeners are the commercially available phenol novolak resins, bisphenol-F, bisphenol-A and resorcinol. The addition of the phenolic resin serves to improve the adhesion strength of the formulation after exposure to moisture and thermal shock at 250° C., and to prevent bleeding of the flexible epoxy out of the formulation.

In general any effective curing catalyst in an effective catalytic amount can be used. The preferred curing catalyst is an imidazole catalyst, and typically is present in an amount of about 5 parts per hundred parts resin. Preferable imidazole catalysts are imidazole, 2-ethylimidazole, 2-ethyl-4-methylimidazole, 2-phenylimididazole, 2-phenyl-4-methylimidazole, and 2-undecylimidazole.

The filler may be any of the thermally or electrically conductive materials known to be suitable for microelectronics applications, used in any effective amount. For many applications, the preferred filler is silver flakes, although other electrically or thermally conductive fillers or silica may be used, and is preferably present in an amount of about 25% by volume of the adhesive formulation.

EXAMPLES

The following examples illustrate the preparation of representative olefinic precursors (ADDUCTS) by the two preferred synthetic routes, and the epoxidation of the olefins by the three preferred epoxidation methods to give the corresponding epoxy compounds (EPOXIES). The evaluation test methods are given and the performance results tabulated.

The examples also disclose snap-curable die attach adhesive formulations that contain the flexible epoxies and the O-glycidyl ether aromatic epoxies, and formulations containing the phenolic resin hardeners.

Test Methods

The following test methods were used to evaluate the sample epoxy resins.

The epoxy equivalent weight (WPE, weight per epoxy) for each of the epoxy products was determined by dissolving the compound in glacial acetic acid followed by titration with standardized H Br/acetic acid (~0.1N) to the violet/green transition of crystal violet indicator.

The viscosity of each of the samples was determined using a Brookfield cone-n-plate viscometer at multiple spindle speeds at 25° C. and is reported as an average of three readings.

The amount of hydrolyzable chlorine was determined by the following method: Weigh accurately 1–5 g (to the nearest 0.1 mg) of resin into a clean, 125 ml Erlenmeyer flask with a Teflon® coated magnetic stir bar. Add 40 ml of 0.1N KOH dissolved in methanol. Place flask fitted with reflux condensor into a water bath heated by magnetic stirrer/hot plate unit. Reflux the stirred solution for exactly 15 minutes, then remove the flask, and allow it to cool to room temperature. Transfer the liquid into a clean 250 ml beaker. Rinse the sample flask three times with 50 ml portions of methanol, transferring the liquid into the beaker. Add 10 ml of glacial acetic acid and titrate the chloride ion potentiometrically to the end point with 0.005N AgNO$_3$ solution. Calculate the hydrolyzable chloride content in ppm as follows:

$$\text{Chloride (ppm)} = \frac{\text{(ml titrant)(N AgNO}_3\text{)(3.55} \times 10^4\text{)}}{\text{weight sample g}}$$

The amount of total chlorine was determined by the following method: Accurately weigh 1–5 g (to the nearest 0.1 mg) of resin into a clean Erlenmeyer flask with a magnetic stir bar. Add 30 ml of dioxane and 15 ml of 3N KOH solution in ethanol. Place flask fitted with a reflux condensor into a 100° C. water bath heated on a stirrer/hot plate unit. Allow sample solution to reflux for 30 minutes. Remove flask and allow it to cool to room temperature. Transfer the liquid into a clean 400 ml beaker. Rinse the sample flask three times with 50 ml portions of methanol, transferring the liquid into the beaker. Add 100 ml of glacial acetic acid. Titrate potentiometrically with 0.005N AgNO$_3$ solution to the end point using a silver electrode with a KNO$_3$ salt bridge. Calculate the chloride content in ppm as described above.

Example I

Syntheses of the Olefinic Precursors

ADDUCT A:

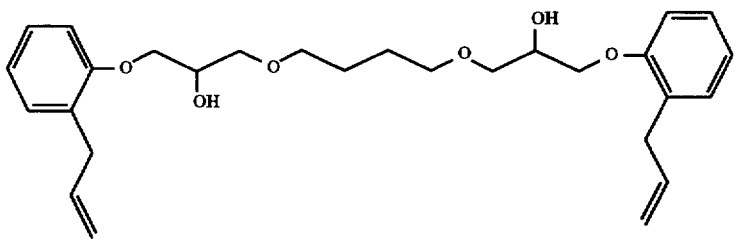

The reaction apparatus was a 500 ml round bottom flask equipped with a mechanical stirrer, thermometer, and condenser. The reagents, 2-allyl phenol (159 gms, 1.19 moles), 1,4-butanediol diglycidyl ether (120 gms, 0.59 moles), and 1% tetramethylammonium chloride catalyst (2.5 gms), were added to the reaction apparatus and stirred at 50° C. for approximately an hour. The temperature was raised to 70° C. and the reagents stirred at that temperature for an additional hour; then the temperature was raised to 120° C. and the reagents held at that temperature while progress of the reaction was monitored by gas chromotograpy (GC). Completion was determined to occur after four hours, at which time the reaction was cooled and the work-up initiated.

The reaction mixture was transferred to a single neck flask and placed on a kugelrohr apparatus (120° C./0.1 mmHg) to strip off any residual starting materials (particularly, 2-allyl phenol).

The adduct was transferred to a 1000 ml separatory funnel and dissolved in 300 ml of toluene. This organic phase was washed with 5% sodium carbonate (3×200 mL), 10% sodium sulfate (3×200 mL), and then passed through a neutral alumina pad (~200 mL) rinsed with toluene.

The toluene was stripped off by rotory evaporator at 60° C./25 mm Hg vacuum, and then placed on a kugelrohr at 70° C./0.1 mm Hg to remove any residual solvent.

The adduct was obtained in 90% yield, and was characterized by IR and $^1$H NMR spectroscopy. It had a viscosity ranging from 650 to 870 cps at 25° C.

ADDUCT B:

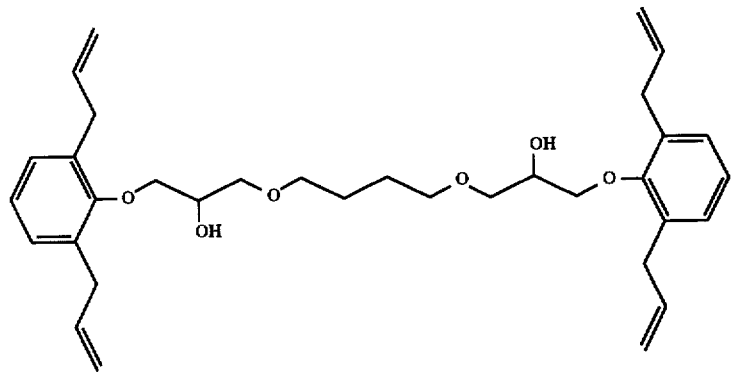

Adduct B was prepared in a manner similar to that used for Adduct A, except that 2,6-diallyl phenol (310 gms, 1.78 moles) was reacted with 1,4-butanediol diglycidyl ether (180 gms, 0.89 moles) in the presence of 4.5 gm tetramethylammonium chloride. The temperature of the reaction mixture was gradually raised to 180° C. and held there for one hour until reaction was complete as indicated by GC. The product was isolated as described for Adduct A in 81% yield and was characterized by IR and $^1$HNMR spectroscopy. It had a viscosity of 983 cps at 25° C.

The reaction apparatus was a one liter multi-neck flask equipped with mechanical stirrer, thermometer, Dean-Stark trap, and condenser. Solid sodium hydroxide pellets (19.95 gm, 0.5 moles) and 83 mL xylene under a gentle nitrogen purge were added to the apparatus and heated with a heating mantle to 70° C. At that temperature 2-allyl phenol (66.9 gm, 0.5 moles) dissolved in 200 mL xylene was introduced through a slow-addition funnel, while the system was brought to reflux. The water formed as a by-product was driven off via azeotropic distillation to the Dean-Stark trap,

ADDUCT C:

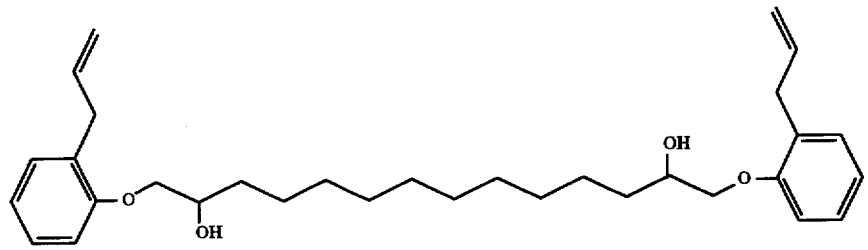

Adduct C was prepared in a manner similar to that used for Adduct A, except that 2-allylphenol (8.44 gm, 0.063 moles) was reacted with 1,2,13,14-diepoxy tetradecane (6.48 gm, 0.0286 moles; prepared by the oxidation of 1,13-tetradecadiene) in the presence of 0.1 gm tetramethylammonium chloride. The reaction mixture was heated to 185° C. and held at that temperature for 3.3 hour until reaction was complete as indicated by GC. The product was isolated as described for Adduct A in 81% yield and was characterized by IR and $^1$HNMR spectroscopy.

followed by distillation of additional xylene (225 mL) through the Dean-Stark trap to remove any trapped water.

Then 125 mL p-cymene, 25 mL dimethylformamide, and 0.1 gm KI were added and the entire contents cooled to 100° C. The dichloride of poly(tetrahydrofuran)-250 (45 gm, 0.17 mole; prepared by the action of thionyl chloride on poly (tetrahydrofuran)-250, which is available from BASF Corp.) dissolved in 50 mL p-cymene was introduced into the flask through a slow-addition funnel. The reaction temperature was raised to 150° C. and held for 24 hours. Upon cooling,

ADDUCT D:

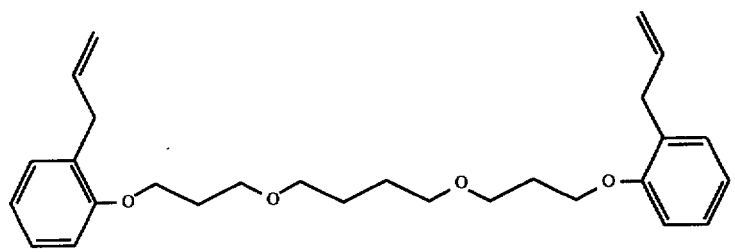

the by-product salts (sodium chloride) were removed by filtration, and the filtrate was washed with 5% sodium hydroxide (2×50 mL), and then 10% sodium sulfate (150 mL each) until the pH became neutral (pH=7 on test strip). The solvent was removed first on a rotory evaporator, then on a Kugelrohr apparatus (130° C./0.2 mm Hg). The product was collected in 95% yield and was analyzed by IR and $^1$HNMR spectroscopy.

ADDUCT E:

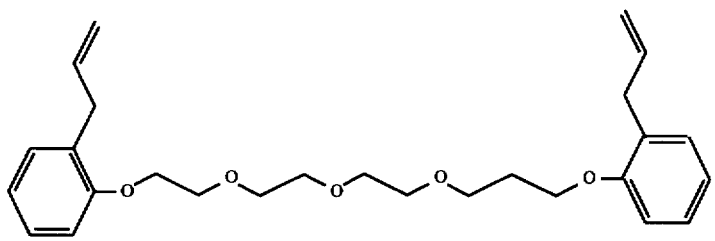

The reaction apparatus was a five liter multi-neck flask equipped with mechanical stirrer, thermometer, Dean-Stark trap, and condenser. Solid sodium hydroxide pellets (79.2 gm, 1.98 moles) and one liter xylene were added to the reaction apparatus under a gentle nitrogen purge, and heated with a heating mantle to 135° C. (reflux). At that temperature 2-allyl phenol (267 gm, 1.98 moles) was introduced through a slow-addition funnel, while the system was maintained at reflux. The water formed as a by-product was driven off via azeotropic distillation to the Dean-Stark trap, followed by distillation of 100 mL additional xylene through the Dean-Stark trap to remove any trapped water.

The internal temperature was lowered to 90° C., and 100 mL dimethylformamide and tetraethylene glycol ditosylate (400 gm, 0.795 moles; prepared by the action of p-toluenesulfonyl chloride on tetraethylene glycol in the presence of pyridine) dissolved in 300 mL xylene were introduced into the flask through a slow-addition funnel. The reaction temperature was raised to 120° C. and held there for two hours. The reaction was cooled and the by-product salts (sodium tosylate) were removed by filtration. The filtrate was washed with 5% sodium hydroxide (2×600 mL), then washed with 10% sodium sulfate (3×300 mL) until the pH became neutral (pH=7 on test strip).

The solvent was removed first on a rotory evaporator, then on a Kugelrohr apparatus (80° C./0.2 mm Hg). The product was collected in 95% yield and analyzed by IR and $^1$HNMR spectroscopy.

Example II

Syntheses of the Epoxy Compounds

EPOXY A:

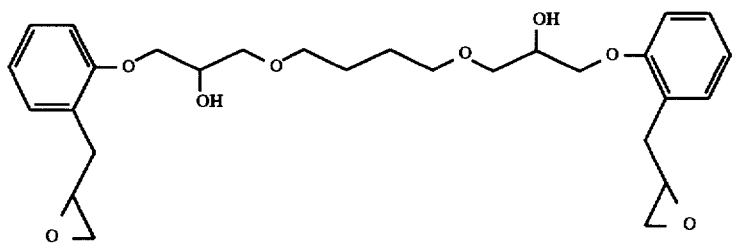

Adduct A was oxidized to give Epoxy A by two methods: with peracetic acid and with peroxyimidic acid.

1. Oxidation with Peracetic Acid

The reaction apparatus was a 500 ml flask equipped with mechanical stirrer, thermometer and slow-add funnel. Adduct A (75 gms, 0.16 moles, 0.32 moles of olefinic functionality), 1,2-dichloroethane (150 mL) and sodium acetate (4.7 gms) was added to the reaction apparatus and brought to 23° C. using a water bath. Introduction of peracetic acid (94.7 gms) (35% in acetic acid) was begun, and the reaction exothermed to 29° C. After addition was completed, the water bath was warmed to 30° C. The internal temperature rose to 38° C. After 10 minutes the temperature dropped to 35° C. and was held steady at 35° C.

for 5 hours. The reaction was monitored for completion by IR spectroscopy for the disappearance or minimization of the 1635 cm$^{-1}$ absorption.

At completion, 300 mL of distilled water was added to the reaction mixture. The phases were separated, and the organic phase washed with 300 mL 5% sodium bicarbonate solution, then with 200 mL of 5% sodium sulfite solution. Toluene (300 mL) was added to break the emulsion. The organic layer was then washed with 200 mL of 10% sodium sulfate, and 200 mL of distilled water.

The organic was separated off, dried over magnesium sulfate and suction filtered. The solvent was stripped off first on the rotory evaporator (50° C./20 mmHg) and then on a Kugelrohr apparatus (60° C./0.1 mmHg). The final product rotory evaporator (40° C./25 mm HG). The residue was taken up in 150 mL toluene and washed with distilled water (150 mL). Emulsification was alleviated by the addition of 10% $Na_2SO_4$. The organic layer was separated and the solvent removed first on a rotory evaporator (80° C./25 mmHg), then on a Kugelrohr apparatus (80° C./0.1 mmHg).

The product was isolated at 74% yield (23.7 gm), characterized by an epoxy equivalent weight=315 (theoretical value=251), viscosity=6270 cps at 25° C., IR, and $^1H$ NMR spectroscopy. Hydrolyzable chlorine=455, and total chlorine=564 ppm.

EPOXY B:

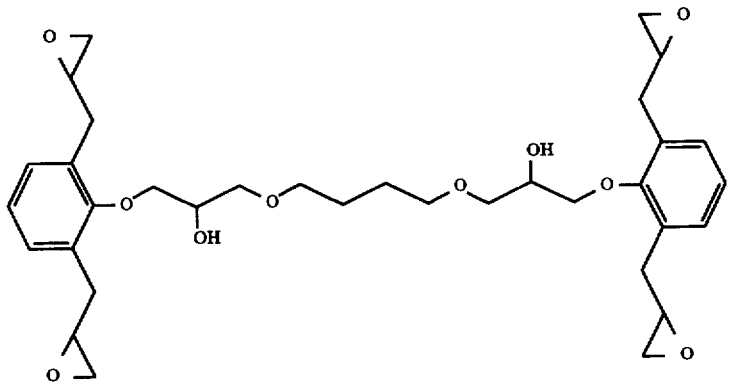

was isolated as an oil, and characterized by a viscosity of 7280 cps at 25° C., an epoxy equivalent weight=269 (theoretical value=251), and by IR and $^1H$ NMR spectroscopy. Total chlorine=717 ppm. In a second preparation of this material the EEW=274, viscosity=6550 cps, hydrolyzable chlorine=519 ppm, and total chlorine=719 ppm.

2. Oxidation with Acetonitrile/Hydrogen Peroxide (Peroxyimidic acid)

The reaction apparatus was a 250 ml round bottom flask equipped with mechanical stirrer, thermometer, and slow-add funnel. Adduct A (30.0 gm, 0.0638 moles, 0.128 moles olefin functionality), methanol (74 mL), acetonitrile (11.54 gm, 0.2815 moles), and $KHCO_3$ (7.12 gm, 0.7111 mole) were added to the apparatus and heated to 40° C. At that temperature 30% $H_2O_2$ (10.0 gm, 0.0882 mole) was added dropwise. The reaction mixture was maintained at 40° C. for seven hours, at which point, additional 30% $H_2O_2$ (13.8 gm, 0.1218 mole) was added dropwise. The reaction was maintained at 40° C. for a further 20 hours.

Then 2,2-dimethoxypropane (48 gm, 0.462 mole, or 0.5 equivalent based on $H_2O$ charged from 30% hydrogen peroxide) was added dropwise. The reaction was heated at 40° C. for an additional 24.5 hours, corresponding to the point at which the IR trace of a reaction sample indicated minimal 1637 cm$^{-1}$ absorbance.

The peroxide was neutralized by the addition of 10% $Na_2SO_3$ as determined by KI-starch indicator test strip. The methanol and acetonitrile were removed in vacuo on the Adduct B was oxidized to give Epoxy B by two methods: with peracetic acid and with peroxyimidic acid.

1. Oxidation with Peracetic Acid

Adduct B was oxidized using 35% peracetic acid as described for the synthesis of Epoxy A. Adduct B (110 gm, 0.2 mole) was treated with peracetic acid (210 mL of 35% solution, 1.09 moles) in 220 mL 1,2-dichloroethane at 35° C. The product was isolated in 85% yield and characterized by an epoxy equivalent weight=176 (theoretical value=154), viscosity=24,300 cps at 25° C., and by IR and $^1H$ NMR spectroscopy. Hydrolyzable chlorine=467 ppm, and total chlorine=620 ppm.

2. Oxidation with Acetonitrile/Hydrogen Peroxide (Peroxyimidic acid)

Adduct B was oxidized using acetonitrile and hydrogen peroxide as described for the synthesis of Epoxy A. The acetonitrile and hydrogen peroxide generated in situ the peroxyimidic acid. Adduct B (150 gm, 0.27 mole) was treated with acetonitrile (97 gm), potassium bicarbonate (60.5 gm), 30% hydrogen peroxide (200 gm), 2,2-dimethoxypropane (812.5 gm), and methanol (375 mL). The reaction was carried out at 40° C. until the IR absorption at 163 cm$^{-1}$ no longer changed significantly. The product was isolated in 74% yield, and was characterized by an epoxy equivalent weight=229 (theoretical value=154), viscosity= 20,900 cps at 25° C., and by IR and $^1H$ NMR spectroscopy. Hydrolyzable chlorine=624 ppm, and total chlorine=839 ppm.

EPOXY C:

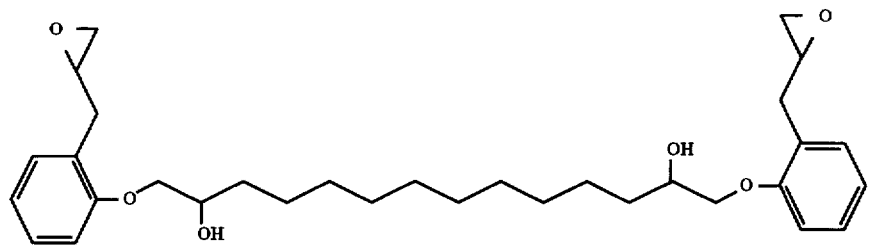

Adduct C was oxidized to give Epoxy C using peroxytungstate catalysis.

Oxidation with Peroxytungstate

Adduct C (17 gm, 0.035 mole) was dissolved in 60 mL dichloroethane to which was added 3.8 gm tetrabutylammonium hydrogen sulfate, and this was stirred vigorously at room temperature. To this rapidly stirred solution was added an aqueous mixture comprising sodium tungstate dihydrate (6.3 gm) in 10 mL distilled water with a sufficient amount of 85% phosphoric acid to adjust the pH to 6.5. Then 30% hydrogen peroxide (15.7 gm, 0.138 mole) was added at room temperature and the combined contents were stirred for 96 hours. At that point, the 1637 $cm^{-1}$ absorption in the IR spectrum was minimized.

The product was isolated by separating the phases and washing the organic layer with 5% sodium sulfite (2×100 mL) until the peroxide was completely quenched. The solvent was removed on a rotory evaporator at a temperature less than or equal to 40° C. and the residue dissolved in 100 mL toluene. The toluene layer was washed with 150 mL 5% sodium carbonate, with water (2×150 mL), then with 10% sodium sulfate (2×150 mL). The toluene was removed from the organic layer first on a rotory evaporator, then on a Kugelrohr apparatus under high vacuum (80° C./0.1 mm Hg). The product was an oil isolated at 93% yield, and was characterized by an epoxy equivalent weight=289 (theoretical value=263), viscosity=9100 cps at 25° C., and by IR and $^1$H NMR spectroscopy. Hydrolyzable chlorine= 883 ppm, and total chlorine=959 ppm.

1. Oxidation with Peracetic Acid

Adduct D (50 gm, 0.107 mole) was oxidized as described in the synthesis of Epoxy A using 35% peracetic acid at 35° C. in 1,2-dichloroethane. The product was isolated as an oil at 60% yield, and was characterized by an epoxy equivalent weight=274 (theoretical value=249), viscosity=417 cps at 25° C., and by IR and $^1$H NMR spectroscopy. Hydrolyzable chlorine=35 ppm, and total chlorine=103 ppm.

2. Oxidation with Peroxytungstate Catalysis

Adduct D (67.8 gm, 0.14 mole) was oxidized as described in the synthesis of Epoxy C using sodium tungstate dihydrate and hydrogen peroxide. The product was isolated as an oil in 83% yield, and was characterized by an epoxy equivalent weight=252 (theoretical value=249), viscosity= 410 cps at 25° C., and by IR and $^1$H NMR spectroscopy. Hydrolyzable chlorine=53 ppm, and total chlorine=100 ppm.

EPOXY D:

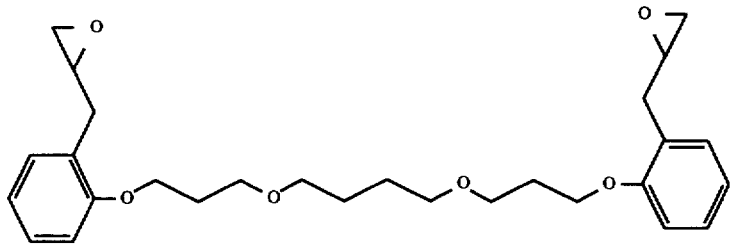

Adduct D was oxidized to Epoxy D by two methods: with peracetic acid and with peroxytungstate catalysis.

ADDUCT E:

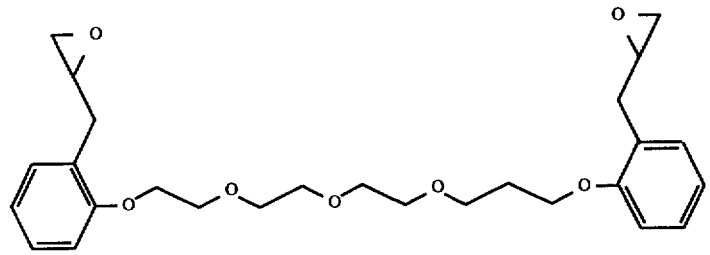

Adduct E was oxidized to Epoxy E by two methods: with peracetic acid and with peroxytungstate catalysis.

1. Oxidation with Peracetic Acid

Adduct E (30 gm, 0.07 mole) was oxidized as described in the synthesis of Epoxy A using 35% peracetic acid at 35° C. in 1,2-dichloroethane. The product was isolated as an oil in 91% yield and was characterized by an epoxy equivalent weight=258 (theoretical value=229), viscosity=397 cps at 25° C., and by IR and $^1$H NMR spectroscopy. In a second preparation of this material the EEW=259, viscosity=354 cps, hydrolyzable chlorine=below detection limits, and total chlorine=785 ppm.

2. Oxidation with Peroxytungstate Catalysis

Adduct E (24 gm, 0.056 mole) was oxidized as described in the synthesis of Epoxy C using sodium tungstate dihydrate and hydrogen peroxide. The product was isolated as an oil in 94% yield, and was characterized by an epoxy equivalent weight=241 (theoretical value=229), viscosity= 347 cps at 25° C., and by IR and $^1$H NMR spectroscopy. Hydrolyzable chlorine=58 ppm, and total chlorine=578 ppm.

mL of toluene was driven off additional to ensure dryness. The organic solution was filtered, neutralized to pH=8 with conc. HCl, and refiltered. The solution was placed in a single-neck round bottom flask and stripped on a rotary evaporator to 60° C./11 mmHg, collecting 300 mL distillate. Further distillation was carried out at atmospheric pressure (~760 mmHg) and 170° C. pot temperature, then establishing vacuum to ~30 mmHg and raising the pot temperature to 219° C. (vapor temperature to 122° C.). The flask was cooled to room temperature.

Preparation of Diglycidyl Ether with Flexible Linkage (example 15): The material was dissolved in 400 g ethanol and 240 mL epichlorohydrin in order to transfer to a 2 liter multi neck flask for the second reaction. This solution was heated to 60° C. at which point the addition of 50% NaOH (1.25 mole) ~70 mL was conducted as prescribed (~7 mL over 25 min., ~10 mL over 5 min., ~46 mL over 35 min., and ~7 mL over 15 min.). The reaction mixture was transferred to a 2-liter single neck flask and ethanol, water, and epichlorohydrin were removed on a rotary evaporator to 96° C./11 mmHg. The residue was dissolved in 600 mL methyl isobutyl ketone and 800 mL water, transferred to a separatory EPOXY F, Comarative example:

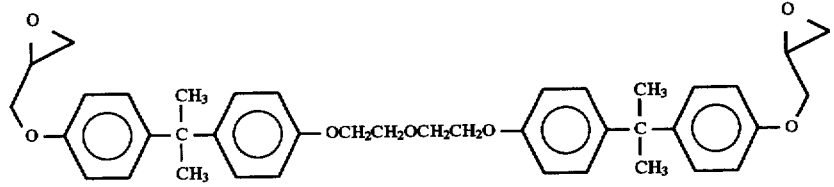

As a comparison to the inventive examples, Epoxy F was prepared according to the methods described in U.S. Pat. No. 3,522,210, issued to Sellers, examples 1A and 15.

Preparation of bisphenol compound (example 1): To a one liter flask with mechanical stirrer, thermometer, slow addition funnel, condenser, and nitrogen blanket was charged bisphenol A (228.29 g, 1.0 mole), 150 g dimethyl sulfoxide (DMSO), and 150 g toluene. After the solid dissolved a solution of 50% aqueous NaOH (80 g, 1.0 mole) was added over 20 minutes. The temperature rose to about 50° C. and heat was applied to raise the temperature to 100°–110° C. Reflux was achieved at 101° C. at which point 2-chloroethyl ether (71.5 g, 58.6 mL, 0.5 mole) was added through the slow addition funnel over 18 minutes. The reaction temperature was held at reflux for 36.75 hours at which point the pH still did not reach 7-8 but GC analysis indicated the reaction had stalled with respect to consumption of bisphenol A. Toluene (150 mL) was added and azeotropic distillation was initiated to drive off ~60 mL H$_2$O and another 40 funnel and the phases separated. The organic layer was washed with 200 mL water, which resulted in an emulsion that was alleviated by the addition of 100 mL saturated sodium sulfate. The pH of the aqueous wash was ~7 (neutral). The organic solution was placed on the rotary evaporator to remove solvent to 95° C./11 mmHg. The material was further stripped on a Kugelrohr apparatus to 133° C./1.5 mmHg. The product, a dark amber material with a stringy taffy-like consistency, was isolated in 89% yield, and was characterized as having an epoxy equivalent weight as WPE=357.5, hydrolyzable chlorine=435 ppm, bound chlorine=2103 ppm, and total chlorine=2538 ppm.

| SUMMATION OF CHLORINE DATA: | | | |
|---|---|---|---|
| EPOXY | Hydrolyzable Chlorine (ppm) | Total Chlorine (ppm) | Bound Chlorine (ppm) |
| A-1 | 519 | 719 | 200 |
| A-2 | 455 | 564 | 109 |
| B-1 | 467 | 620 | 153 |
| B-2 | 624 | 839 | 215 |
| C | 883 | 959 | 76 |
| D-1 | 35 | 103 | 68 |
| D-2 | 53 | 100 | 47 |
| E-1 | none detected | 785 | 785 |
| E-2 | 58 | 578 | 520 |
| F-Comparative | 435 | 2538 | 2103 |

In comparing the inventive epoxy compounds with prior art compound F, it will be noted that the hydrolyzable chlorine content is similar, and it is further noted that there are methods described in the literature for treatment of the epoxide containing molecule to reduce this value. (See, for example, U.S. Pat. No. 4,785,061, which discusses at column 2 hydrolyzable chlorine, bound chlorine, and total chlorine.) Nevertheless, the total chlorine value is critical when considering the prevention of corrosion of sensitive microcircuitry conductive lines, and reported methods lower but do not effectively remove this chlorine contaminant from an epichlorohydrin based synthetic route.

Example III

Flexibility and Strength of Epoxies

The epoxies were tested for modulus, percent strain, radius of curvature as a measure of their flexibility and die shear as a measure of their adhesive strength.

The modulus is a coefficient of elasticity representing the ratio of stress to strain as a material is deformed under dynamic load. These epoxies demonstrated a low modulus, preferably less than or equal to 2.0 MPa. The percent strain is a measure of the resistance to deformation, and these compounds have a percent strain of elongation, greater than or equal to 5%, and notably in certain cases the test specimen yielded.

When formulated with silver flakes and used to bond silicon chips to a metal lead frame substrate, the cured epoxies demonstrated a high radius of curvature, greater than or equal to 350 mm, and good die shear strength, greater than or equal to 13 MPa at room temperature.

The cured $T_g$ values for these epoxies will be 150° C. or less, and for some compounds will be 100° C. or less.

Modulus

The following equipment was used to prepare epoxy plaques for the modulus and percent strain flexural testing: 2 pyrex plates 10×10 3/16" from F.J. Gray Co.; copper wire (23" per test); silcon tubing ID=3/32", OD=5/32", wall=1/32" (~23" per test); aluminum spacers (2"×3/4"×1/8"); binder clips size medium (5/8"); Release ALL #50 from Airtech International, Inc.

To prepare the form for the plaques, two glass (PYREX) plates were cleaned with toluene, then acetone. A thin coat of Release ALL #50 was applied to one side of each plate with a clean rag and allowed to dry for 10 minutes at room temperature. A second coat of Release ALL #50 was applied over the first coat. The plates were dried in a oven at 125° C. for 30 minutes. A 23" length of copper wire was inserted into a 23" length of silicone tubing, and the wire/tube bent into a "U" shape form to fit between the two glass plates as a reservoir for the liquid epoxy formulation before cure. Aluminum spacers were positioned around the edges of the coated side of one glass plate. The wire/tube form was then laid on the coated side of the glass plate, interior to the spacers. The second glass plate, coated side to the wire/tube and spacers, was laid over the first glass plate so that the wire/tubing form and spacers were sandwiched between the two plates. The two plates of glass were clamped together using the binder clips.

A sample of 90.25 g of epoxy resin was poured into a 250 mL single neck flask. The sample was degassed on a Kugelrohr at 70°–75° C. and 0.2 mm Hg for ~20 minutes, and cooled to 50° C. Based on 100 parts by weight of the epoxy, (4.75 gm) 5 parts by weight of 2-ethyl-4-methylimidazole was added with mixing to the sample. The sample was degassed on a Kugelrohr at 50° C. and 2 mmHg for ~20 minutes.

The epoxy sample was poured into the cavity formed by the "U" shaped wire/tube and glass plate mold with care taken to avoid forming air pockets. The poured epoxy sample was cured in a programmable oven in an upright position according to the following program: 50° C. for 30 minutes; 50° C. to 125° C. @ 1° C./min; hold at 125° C. for 1 hour; 125° C. to 175° C. @10° C./min; hold at 175° C. for 1 hour; cool to 60° C. over 90 min.

The resulting epoxy plaques, after release from the mold, were cut into 3"×0.5" pieces with a water-cooled diamond blade saw. The 0.5 cut was cut with a slight excess so that the plaques could then be milled to exactly 0.5".

Flexural testing was carried out on the plaques using an Instron 4507 at room temperature in the three point bend mode following ASTM method D790-84a. Data from these experiments is reported in the following Table as Young's Modulus in MPa units, % strain, and $T_g$ (peak in Tan delta) in °C. units.

Die Shear

Each epoxy (to which was added 5 parts 2-ethyl-4-methyl imidazole as curing catalyst to 100 parts by weight epoxy) was mixed with silver flake at 25% volume until the silver was fully wetted out. The mixture was degassed under vacuum at room temperature for 15–20 minutes, and then allowed to sit at room temperature with frequent stirring for 60 minutes.

Silicon chips (80×80 mil$^2$) were coated on one side with the adhesive formulation and placed on a copper lead frame (D/L) and cured in a 175° C. oven for one hour. The samples were tested after cure for die shear strength at room temperature (RT). Die shear strength was measured using a Hybrid Machine Products Corp. die shear tester (Model 1750)/Chatillon DFI 50 digital force gauge. The force required to remove the bonded die was read in kg units, and converted to a die shear strength in MPa averaged over ten samples.

Preferred die shear values are those of 13 MPa or greater.

Radius of Curvature

Each epoxy to be tested was prepared, degassed, and aged for one hour as described above in the die shear test method. Silicon chips (200×600 mil$^2$) were coated with adhesive on one side and placed on a lead frame and cured in a 175° C. oven for one hour. The radius of curvature for the cured samples was measured using a Tokyo Seimitsu SURFCOM surface texture measuring instrument and reported in millimeter (mm) units, averaged over three samples. Preferred radius of curvature values are those of 350 mm or greater.

Control Epoxies

The control epoxy resins were the following:

Bisphenol F diglycidyl ether, sold under the tradename EPICLON 830S, a product of Dai Nippon, having the structure:

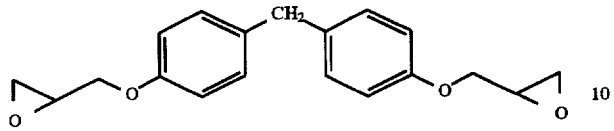

Bisphenol A diglycidyl ether, sold under the tradename EPON 828, a product of Shell Corporation, having the structure:

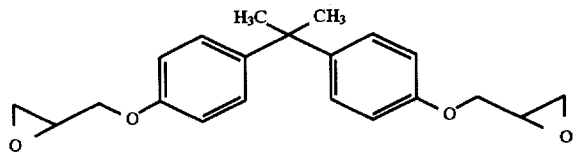

A dimer acid diglycidyl ester, sold under the tradename EPON 871, a product of Shell Corporation, having the structure:

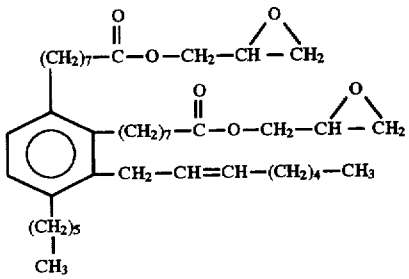

A polyglycol diepoxide, sold under the tradename DER 732, a product of Dow Corporation, having the structure:

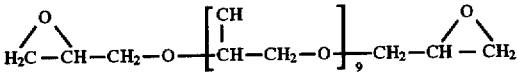

Performance Results

Epoxies A–E were tested according to the test methods described above and compared to the control aromatic epoxy resins and epoxy resins containing flexibilizers. The results of the flexibility and strength performance tests, and comparisons to the control epoxies are presented in the following table. The inventive flexible epoxies demonstrated a low modulus and high percent strain compared to the controls. Notably, a few of the flexible epoxies yielded during the strain testing, in contrast to the controls, all of which snapped.

All of the inventive epoxies and the aromatic control epoxies showed a high adhesive strength, and in some cases very high radius of curvature. The EPON 871 epoxy resin and DER 732 epoxy resin controls, which are based on reactive flexibilizers, do present high radius of curvature values, but suffer from low die shear strengths.

The control blend of EPON 871 epoxy resin (a reactive flexibilizer) and the aromatic Bisphenol F epoxide shows good die shear strength, but this is achieved at the expense of a loss of flexibility as indicated by the radius of curvature value.

| Epoxy Compounds | Cure Agent | Modulus (GPa) | % Strain | Tg °C. (Tan δ) | Die Shear (MPa) | ROC (mm) |
|---|---|---|---|---|---|---|
| Epoxy A | a | 1.72 (+/−0.28) | 5.5 yielded | 67 | 21.6 | 348 |
| Epoxy B | a | 3.07 (+/−0.10) | 6.4 | 110 | 29.8 | 266 |
| Epoxy C | a | 0.37 | 8.3 yielded | 54 | 22.5 | 377 |
| Epoxy D | b | — | — | — | 19.7 | 698 |
| Epoxy E | b | — | — | — | 19.9 | 493 |
| Controls | | | | | | |
| Bisphenol F diglycidyl ether | a | 3.10 (+/−0.07) | 5.4 | 151 | 26.8 | 213 |
| Bisphenol A diglycidyl ether | a | 2.69 (+/−0.01) | 3.9 | 174 | 31.8 | 324 |
| EPON 871/Bisphenol F diglycidyl ether 70:30 | a | | | | 17.3 | 288 |
| EPON 871 | | | | | 5.2 | 1354 |
| DER 732 | | | | | 1.4 | 1682 |

Cure catalyst:
a = 2-ethyl-4-methyl imidazole, 4–6 pphr (parts per hundred parts resin); cure
b = phenol novolac (HRJ-1166 from Schenectady Chemical), 10 pphr and 2-ethyl-4-methyl imidazole, 4 pphr

Example IV

Snap-cured Adhesive Formulations

Inventive epoxies C, D, and E, and a proprietary flexible epoxy, designated EPOXY X, were formulated into die attach adhesives comprising by weight 80 parts of flexible epoxy and 20 parts aromatic O-glycidyl ether, and 20 or 40 parts per hundred parts of epoxy resin (pphr) of a phenolic hardener. The curing agent was 5 pphr of 2-ethyl-4-methyl imidazole.

EPOXY X is a proprietary flexible diepoxy synthesized from dimer acid and having a 36 carbon chain between two epoxy end groups.

The aromatic epoxies were:

A bisphenol-F epoxy resin, sold under the tradename EPON 862, a product of Shell Chemical Company, having the structure:

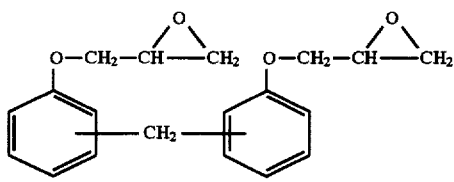

A proprietary epoxy resin, designated EPOXY Y, having the structure:

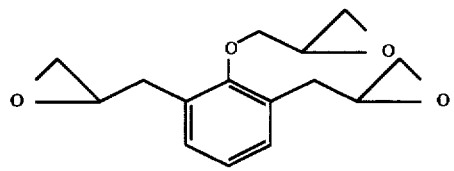

The phenolic hardener was a phenolic novolak resin sold under the tradename HRJ-1166 from Schenectady Chemical having the structure:

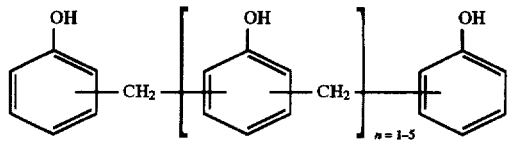

Preparation of the formulations was as follows: the phenolic hardener resin was dissolved at 130° C. in the flexible epoxy; the imidazole catalyst was dissolved in the aromatic epoxy; these two mixtures were blended and the blend mixed with 25% by volume silver flakes.

These formulations, and a control die attach similar to those commercially available, were used to bond 80×80 mil$^2$ and 200×600 mil$^2$ silicon dies to copper lead frames. These assemblies were snap-cured on a hot plate at 225° C. for one minute, and were fully cured as determined by DSC analysis.

The adhesive formulations were tested for die shear strength and radius of curvature as described in Example III. The die shear tests were run on the 80×80 mil$^2$ die after cure (i) at room temperature (RT), (ii) at 250° C. after heating at 250° C. for one minute (250° C./1 min) (to simulate the wire bonding operation during manufacture), and (iii) after boiling in water for two hours, and then at 250° C. after heating at 250° C. for one minute (100° C. H$_2$O; 250° C./1 min) (intended to test resistance to moisture and the phenomenon known as "pop-corn," a mechanical failure of fully encapsulated packages after moisture exposure during solder reflow process, 220°–260° C.).

Results are presented in the following table and show that the snap-cured formulations containing the inventive flexible epoxies maintain their flexibility and good die shear strength at room temperature and after being thermally shocked. The die shear strength after exposure to moisture and thermal shock are within a range acceptable for use as die attach adhesives.

| SNAP CURE FORMULATION | | | DIE SHEAR (MPa) | | | RADIUS OF CURVATURE | |
|---|---|---|---|---|---|---|---|
| | | | | 100° C. | | | |
| Composition parts by - weight | Epoxy Properties | RT | 250° C., 1 min | H$_2$O, 2 hr 250° C., 1 min | RT | 250° C./1 min |
| EPOXY C 80 | Tg = 60° C. WPE = 289 | 23.7 cohesive failure | 1.4 cohesive failure | 1.1 cohesive failure | 420 mm | 350 mm |
| EPON 862 20 Novolak 20 | V = 9100 cps | | | | | |
| EPOXY D 80 | Tg = 52° C. WPE = 252 | 14.3 cohesive failure | 1.4 cohesive failure | 1.2 cohesive failure | 480 mm | 420 mm |
| EPON 862 20 Novolak 40 | V = 410 cps | | | | | |
| EPOXY E 80 | Tg = 60° C. WPE = 241 | 23.7 cohesive failure | 1.5 cohesive failure | 1.2 cohesive failure | 400 mm | 380 mm |
| EPON 862 20 Novolak 40 | V = 347 cps | | | | | |
| FLEX EPOXY X 80 | Tg = 28° C. WPE = 376 | 17.7 cohesive failure | 1.2 cohesive failure | 0.8 cohesive failure | 550 mm | 470 mm |
| EPON 862 | V = 361 cps | | | | | |

-continued

| SNAP CURE FORMULATION | | DIE SHEAR (MPa) | | | RADIUS OF CURVATURE | |
|---|---|---|---|---|---|---|
| Composition parts by - weight | Epoxy Properties | RT | 250° C., 1 min | 100° C. H₂O, 2 hr 250° C., 1 min | RT | 250° C./1 min |
| 20 Novolak 40 FLEX EPOXY X 80 AROM EPOXY Y 20 Novolak 40 | Tg = 28° C. WPE = 376 V = 361 cps | 14.3 cohesive failure | 2.0 cohesive failure | | 320 mm | 320 mm |
| Control | | 23.7 | 2.1 | 0.2 | 230 mm | 220 mm |

Notes:
(a) The epoxy equivalent weight (WPE, weight per epoxy) for each of the epoxy products was determined by dissolving the compound in glacial acetic acid followed by titration with standardized HBr/acetic acid (~0.1N) to the violet/green transition of crystal violet indicator.
(b) The viscosity of each of the samples was determined using a Brookfield cone-n-plate viscometer at multiple spindle speeds at 25° C. and is reported as an average of three readings.

We claim:

1. A flexible epoxy compound, characterized in that it has a total chlorine content of less than 0.1% by weight, having the structural formula:

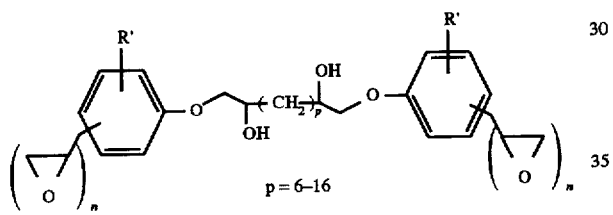

in which:

R' is H, $C_{1-18}$alkyl, $C_{1-5}$alkoxy or aryl or alkylaryl, $C_{1-5}$perfluoroalkyl, or $C_{1-5}$acyl; and n is an integer 1–3; and p is an integer 6–16.

2. A flexible epoxy compound according to claim 1 having the structure:

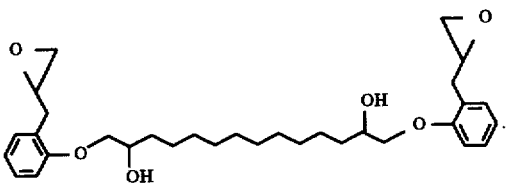

3. An adhesive for use in microelectronics applications containing a flexible epoxy compound according to claim 1.

* * * * *